US006797462B1

(12) United States Patent
Kappes et al.

(10) Patent No.: US 6,797,462 B1
(45) Date of Patent: Sep. 28, 2004

(54) CELL-BASED ASSAY FOR IMMUNODEFICIENCY VIRUS INFECTIVITY AND SENSITIVITY

(75) Inventors: John C. Kappes, Birmingham, AL (US); Xiaoyun Wu, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/719,340

(22) PCT Filed: Jun. 23, 1999

(86) PCT No.: PCT/US99/14104

§ 371 (c)(1),
(2), (4) Date: Apr. 13, 2001

(87) PCT Pub. No.: WO99/67429

PCT Pub. Date: Dec. 29, 1999

Related U.S. Application Data

(60) Provisional application No. 60/090,317, filed on Jun. 23, 1998.

(51) Int. Cl.[7] .......................... C12Q 1/70; G01N 33/53; C12N 5/00; C12N 7/02; C12N 5/08
(52) U.S. Cl. .............................. 435/5; 435/22; 435/239; 435/325; 435/367
(58) Field of Search ........................... 435/5, 7.2, 7.23, 435/239, 325, 367, 6, 7.24, 372.3

(56) References Cited

U.S. PATENT DOCUMENTS

| 5,026,635 | A | | 6/1991 | Ferguson |
| 5,110,906 | A | | 5/1992 | Maddon |
| 5,126,433 | A | | 6/1992 | Maddon |
| 5,422,274 | A | | 6/1995 | Maddon |
| 5,443,954 | A | * | 8/1995 | Reddel et al. ............. 435/7.21 |
| 5,532,124 | A | | 7/1996 | Block et al. |
| 5,670,324 | A | | 9/1997 | Littman |
| 5,800,986 | A | | 9/1998 | Haseltine et al. |
| 5,811,282 | A | | 9/1998 | Chesebro |
| 5,817,767 | A | | 10/1998 | Allaway |
| 5,837,464 | A | | 11/1998 | Capon et al. |
| 6,025,154 | A | | 2/2000 | Li et al. |
| 6,258,527 | B1 | * | 7/2001 | Littman et al. ................ 435/5 |
| 2002/0037281 | A1 | | 3/2002 | Davidson et al. |
| 2002/0037498 | A1 | | 3/2002 | Hallowitz et al. |

FOREIGN PATENT DOCUMENTS

| WO | WO 96/19495 A1 | 6/1996 |
| WO | WO 97/28258 A1 | 8/1997 |
| WO | WO 98/00535 | 1/1998 |
| WO | WO 99/23107 | 5/1999 |
| WO | WO 00/65356 A1 | 11/2000 |

OTHER PUBLICATIONS

Splenlehauer et al. Virology. 2001; 280: 292–300.*
Roos et al. Virology. 2000; 273: 307–315.*
Chackerian et al. Journal of Virology. 1997; 71 (5): 3932–3939.*
Lan, Y., et al., "A Direct Test for Zidovudine (ZDV) Resistance in Clinical Isolates of HIV," Int. Conf. AIDS 1993, vol. 9, No. 1, pp. 476, Abstract No. PO–B26–2048.
Chackerian, B., et al., "Human Immunodeficiency Virus Type 1 Coreceptors Participate in Postentry States in the Virus Replication Cycle and Function in Simian Immunodeficiency Virus Infection," *Journal of Virology*, May 1997, pp. 3932–3939, vol. 71, American Society for Microbiology, USA.
James, J., "T–20 and Trimeris", *Aids Treatment News*, Apr. 1998, pp. 1–6.
Kilby, M., et al., "Potent Suppression of HIV–1 Replication in Humans by T–20, a Peptide Inhibitor of gp41–Mediated Virus Entry," *Nature Medicine*, 1998, pp. 1302–1307, vol. 4 (11).
Kuhmann, S., et al., "Polymorphisms in CCR5 Genes of African Green Monkeys and Mice Implicate Specific Amino Acids in Infections by Simian and Human Immunodeficiency Viruses," *Journal of Virology*, Nov. 1997, vol. 71(11), American Society for Microbiology.
Maddon, P., et al., The Isolation and Nucleotide Sequence of a cDNA Encoding the T Cell Surface Protein T4: A New Member of the Immunoglobulin Gene Family, *Cell*, 1985, pp. 93–104, vol:42, College of Physicians and Surgeons, New York.
Platt, E., et al., "Effects of CCR5 and CD4 Cell Surface Concentrations on Infections by Macrophagetropic Isolates of Human Immunodeficiency Virus Type 1," *Journal of Virology*, 1998, pp. 2855–2864, American Society for Microbiology.
Raport, C., et al., "Molecular Cloning and Functional Characterization of a Novel Human CC Chemokine receptor (CCR5) for RANTES, MIP–1β, and MIP–1α," *Journal of Biological Chemistry*, 1996, pp. 17161–17166, vol. 271(29), The American Society of Biochemistry and Molecular Biology, Inc. USA.

(List continued on next page.)

*Primary Examiner*—Shanon Foley
(74) *Attorney, Agent, or Firm*—Alston & Bird LLP

(57) ABSTRACT

Methods and reagents for the capture of primary HIV are provided. A cell line expressing CCR5, CXCR4 and CD4 receptors binds and is infected by primary HIV. The cell line contains a marker gene sequence, the marker gene sequence expressed in near linear quantities over at least two orders of magnitude in response to HIV infection. Primary HIV is amplified to create a primary virus stock through insertion of an amplicon gene into the receptor expressing cell line. HIV amplification occurs rapidly and is operative with noninfectious HIV through amplification in the presence of an infectivity complement. The present invention is useful in determining host HIV titer, drug sensitivity, HIV amplification, gene sequencing and co-receptor utilization.

7 Claims, 9 Drawing Sheets

OTHER PUBLICATIONS

Rimsky, L., et al., "Determinants of Human Immunodeficiency Virus Type 1 Resistance to gp41–Derived Inhibitory Peptides," *Journal of Virology,* 1998, pp. 986–993, vol. 72 (2), American Society for Microbiology.

Black, R., et al., "Comparison of Methodologies for Detecting HIV Resistance," Int. Conf. AIDS, 1991, Abstract No. W.A. 1078.

Japour, L., et al., "A Direct Test for Zidovudine (ZDV) Resistance in Clinical Isolates of HIV," Int. Conf. AIDS, 1993, Abstract No. PO–B26–2048.

Jackson, C., et al., "Stavudine Sensitivities in Clinical HIV Isolates Obtained from a Pediatric Population," American Pediatric Association and Society for Pediatric Research Annual Meeting, May 6–10, 1996, unnumbered abstract.

Wei, X., et al., "HIV–1 Selection in Response to Inhibition of Virus Fusion and Entry," Abstract 611.

Deichmann, M. et al., "Expression of the Human Immunodeficiency Virus Type–1 Coreceptors CXCR–4 (fusin, LESTR) and CKR–5 in CD34+ Hematopoietic Progenitor Cells," *Blood,* 1997, pp. 3522–3528, vol. 89(10).

D'Souza, M. and Harden, V., "Chemokines and HIV–1 Second Receptors," *Nature Medicine,* 1996, pp. 1293–1300, vol. 2(12).

Hasler, J., et al., "A Rapid, Quantitative Bioassay Based on the Human Immunodeficiency Virus *Trans*–Activator," *Aids Research and Human Retroviruses*.1989, p. 507–516, vol. 5(5).

Moore, J., et al., "Co–receptors for HIV–1 Entry," *Current Opinion in Immunology,* 1997, pp. 551–562, vol. 9(4).

Zella, D., et al., "Interferon–γ Increases Expression of Chemokine Receptors CCR1, CCR3, and CCR5, But Not CXCR4 in Monocytoid U937 Cells," *Blood,* 1998, pp. 4444–4450, vol. 91(12).

* cited by examiner

CELL-BASED ASSAY FOR IMMUNODEFICIENCY VIRUS INFECTIVITY AND SENSITIVITY

This application is U.S. national stage application of PCT International Application No. PCT/US99/14104 filed Jun. 23, 1999, which claims priority to provisional application 60/090,317, filed Jun. 23, 1998, now abandoned.

FIELD OF THE INVENTION

The present invention relates genetically modified cells, to an assay and methods and the usage thereof to measure the infectivity and viral resistant/sensitivity of isolate from peripheral blood mononuclear cells (PBMC) and plasma of an immunodeficiency virus. The present invention has utility in determining the HIV co-receptor usage, discovery of new drugs effective against HIV and monitoring a drug therapy protocol in order to enhance the effectiveness of drug treatment regimes against HIV-1 infection,

BACKGROUND OF THE INVENTION

There is currently no cost effective, "high throughput" method for analyzing the drug resistant phenotype of primary virus isolates derived from individuals receiving antiretroviral treatment. Various in vitro biologic and immunologic techniques have been developed to detect human and simian immunodeficiency viruses (HIV and SIV, respectively). These include assays that detect the enzymatic activity of the reverse transcriptase (RT) protein, ELISA based assays for the detection of HIV/SIV core antigen (HIV-1 p24 or HIV-2/SIV p27), direct quantitation of infectious virus by syncytial focus plaque assays or limiting dilution titration in susceptible host cells, visualization of virions by electron microscopy, in situ hybridization, and various nucleic acid-based assays. Recently, genetic reporter-based assays have been created to detect HIV/SIV infection. In this approach, mammalian cells are genetically modified to express a reporter gene such as β-galactosidase (β-gal), green fluorescent protein (GFP) or chloramphenicol acetyltransferase (CAT) in response to infection and Tat protein expression. These detection systems require enumeration of the number of infection-positive cells by flow cytometry or fluorescence microscopy (GFP), microscopy (β-gal), or the utilization of radioisotopes (CAT). The firefly luciferase gene, under control of the HIV-1 LTR promoter, has been used as a reporter gene for HIV-1 infection. Luciferase is very sensitive marker gene for HIV-1 infection, since expression of a relatively few number of luciferase molecules can result in appreciable activity levels using standard luciferase detection assays.

The sensitive detection of the virus quasispecies that comprise primary HIV isolates has proved difficult using immortalized CD4 positive cell lines. At least in part, this has been due to the lack of expression of the CCR5 chemokine co-receptor on the surface of such cell lines. The failure to detect infection of primary virus isolates (T-cell and macrophage tropic viruses) using immortalized cell lines has greatly impeded the development of useful approaches for detecting, quantifying and analyzing HIV infection of primary virus isolates. The present invention largely overcomes the prior art limitations.

SUMMARY OF THE INVENTION

Figure 1:
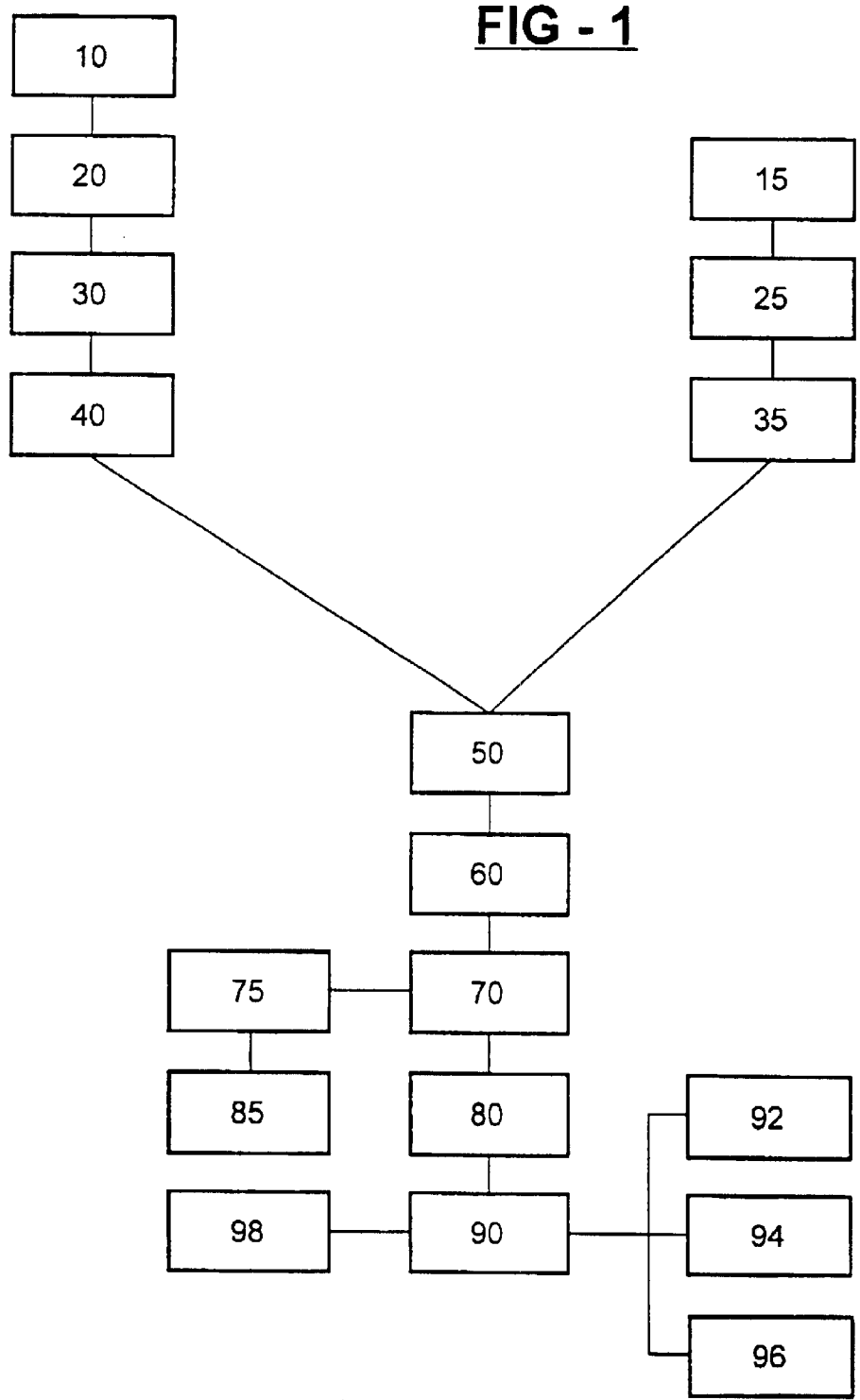
FIG. 1 is a schematic block diagram illustrating a generalized sequence of steps in creating an assay for detecting and analyzing primary HIV.
Figure 2A:
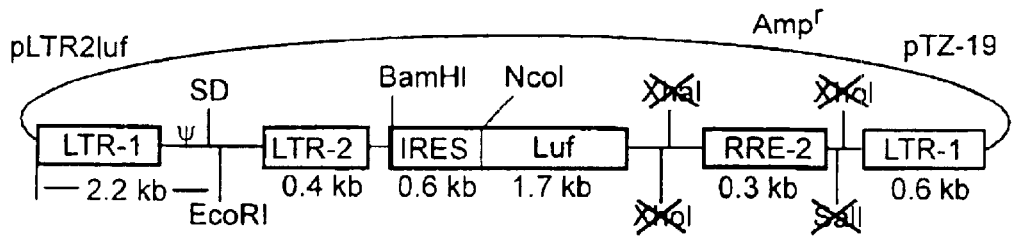
FIGS. 2A–2E are schematics illustrating the construction of various gene transfer expression plasmids of the present invention.
Figure 2B:
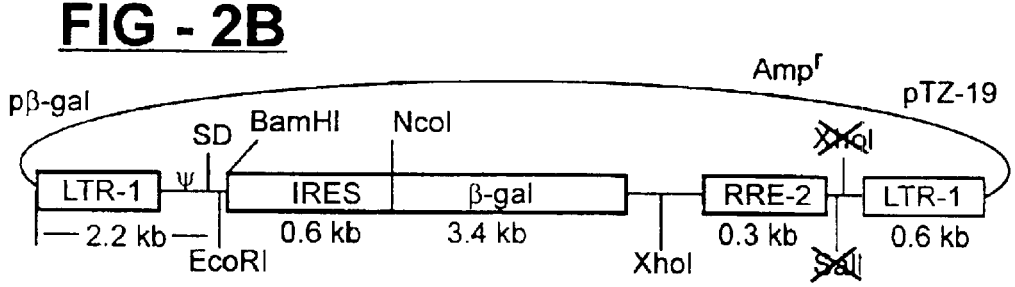
Figure 2C:
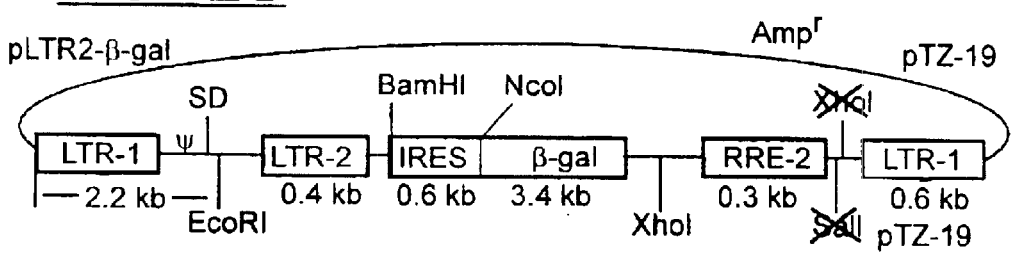
Figure 2D:
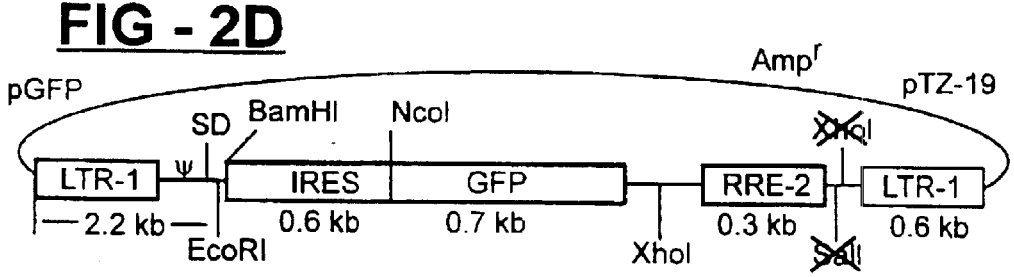
Figure 2E:
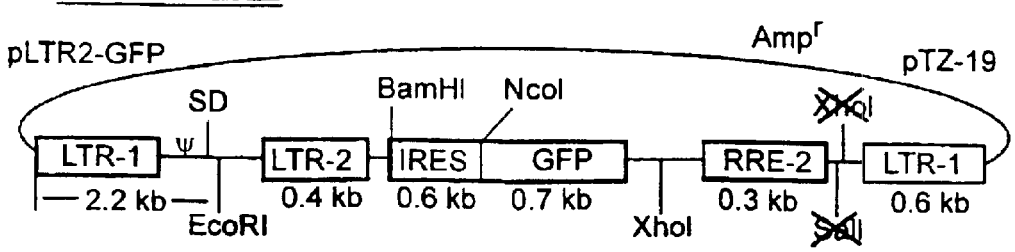

The present invention pertains to a cell-based assay for analyzing primary HIV including an immortalized cell line that expresses the CCR5, CXCR4 and CD4 receptors and a marker gene. The CCR5 or CD4 receptors enable binding and entry of HIV wherein marker gene expression correlates the magnitude of virus infection. An immortalized cell line is disclosed capable of allowing efficient amplification of primary HIV. A method is further disclosed wherein the cell line contains a gene that can be expressed in response to infection of the virus. A method is further disclosed for producing an immunodeficiency virus infection sensitive clonal cells, the method including selecting a cell line expressing CCR5, CXCR4 and CD4, thereafter transducing the cell line with a gene vector encoding for a marker gene such as luciferase such that marker gene expression correlates to the magnitude of immunodeficiency virus binding by said cell line and establishing sensitive clonal cells therefrom.

The present invention finds utility as a method for detecting, isolating and analyzing primary HIV by infecting a cell line of the present invention with a quantity of virus and after some time measuring marker gene expression. Practicing the method of the present invention for determining immunodeficiency virus titer and conducting the presence of a drug candidate indicates the sensitivity of a given strain, type, species or genus of virus to the given drug candidate. The present invention affords the ability to test virus derived from blood plasma as well as cell culture.

DESCRIPTION OF THE INVENTION

The use of an immortalized cell line to detect and analyze primary HIV other than PBMC offers numerous advantages which are exploited to develop a novel assay. Currently, one of the major limitations is that immortalized cell lines are refractory to primary HIV. The expression of CCR5 in an immortalized cell line significantly enhances the detection of primary HIV-1. The ability to detect primary isolates of HIV-1 with greater sensitivity than currently possible is an aspect of the present invention. Unlike previous assays, the present invention provides for: (1) the sampling and analysis of a representative population of viruses that comprise primary HIV-1; (2) the analysis of a significantly greater proportion of virus; and (3) high throughput testing, via miniaturization and sampling of small sample volumes.

The J53-C13 cell line of the present invention were deposited with the Patent Depository of the American Type Culture Collection (ATCC), Manassas, Va., 20108 on Nov. 25, 2003 and assigned Patent Deposit No. PTA-5659. This deposit will be maintained under the terms of the Budapest Treaty on the International Recognition of the Deposit of Microorganisms for the Purposes of Patent Procedure. This deposit was made merely as a convenience for those of skill in the art and are not an admission that a deposit is required under 35 U.S.C. §112.

Most prior art molecular clones of HIV-1 have been derived by tissue culture methods that select for viruses that do not require CCR5 co-receptor for infection, herein defined as T-tropic viruses. Such clones are not able to infect monocytes and macrophages. The term "T-trophic virus" is intended herein to define a phenotype of an immunodeficiency virus capable of infecting a T-cell by binding the CD4 receptor on the T-cell. The term "macrophage trophic virus" is intended to mean a phenotype of an immunodeficiency virus capable of infecting a macrophage by binding the CCR5 co-receptor on the macrophage. This difference in tropism has been mapped to the viral env gene. The SG3 (S. K. Ghosh et al. 1993, Virology 194:858–864) and NL43 (W. Paxton et al. 1993, J. Virol. 67:7229–7237) strains of HIV-1 are derived by extensive passage in tissue culture. They represent T-cell tropic viruses and do not infect monocytes and macrophages. These viruses are not representative of the complex mixtures of viruses that exit in infected individuals. Primary HIV-1 represent virus that is derived directly from the blood of an HIV infected individual. Primary HIV can also be derived by short term culture in vitro culture in primary peripheral blood mononuclear cells (PBMC). Primary HIV can also be derived using the cell line of this invention. Such isolates are complex mixtures and may contain macrophage- and/or T-tropic viruses. During the natural history/progression of HIV-1 infection there is generally a shift from a population of macrophage-tropic toward one of T-tropic viruses. T-cell tropic viruses are able to infect cells that express CD4 and CXCR4, while macrophage tropic (M-tropic) viruses also require expression of the CCR5 chemokine co-receptor. Most HIV-2 and SIV viruses also require the CCR5. Several groups have produced cell lines that express CD4, CXCR4 and CCR5 in attempts to render them sensitive to infection with primary HIV-1 (both T-cell and macrophage tropic viruses). Only recently have such cell lines been derived which appear to be susceptible to infection with diverse HIV-1 isolates (Platt et al., J. Virol. 72:2855, 1988; Overbaugh et al., J. Virol. 71:3932, 1997).

As used herein, "primary HIV" is defined as HIV derived directly from an infected host organism from sources such as blood, plasma, PBMC, CSF and other tissues.

As used herein, "immunodeficiency virus" is defined as various strains and stocks of HIV-1, HIV-2, SIV and lentiviruses.

As used herein, "minor population" is defined as a titer of a given viral strain, type or species or genus that constitutes less than 10% of the total quantity of virus present obtained from a host culture or organism.

As used herein, "major population" is defined as the numerically dominant viral strain, type, species or genus of a viral titer obtained from a host culture or organism.

As used herein, "drug sensitivity" is defined as the effectiveness of a drug to inhibit HIV replication and/or expression with a host cell, the term is used synonymously with "drug resistivity."

By making genetic modifications to a CCR5 or CD4 expressing cell line, the present invention represents is an efficient method for analyzing the drug sensitivity properties of primary HIV, such as HIV-1.

FIG. 1 is a schematic block diagram illustrating a generalized sequence of steps in creating an assay for measuring HIV-1 drug sensitivity according to the present invention. The creation of a cell based assay of the present invention involves a series of steps. Initially, a vector is constructed for the purpose of transducing mammalian cells with a marker gene. Such a marker gene transduction plasmids bring the marker gene expression under the regulation of an immunodeficiency virus 10. Preferably, the marker gene vector is placed under the control of HIV-1 or HIV-2 long terminal repeats (LTRs) and the Rev responsive element (RRE). The marker genes illustratively including β-gal, luciferase, GFP, CAT and other fluorescent proteins. Preferably, the marker gene is luciferase. CD4 positive cells are then transduced with the vector in order to confirm appropriate marker gene expression from the transduction vectors 20. Preferably, the cells are CD4, CCR5, CXCR4 positive. It is appreciated that an amplicon gene is readily substituted for a marker gene to induce amplification of viral stocks (not shown). Preferably, the amplicon gene is Tat.

Clones of the stable CD4 positive cell line are established 30. A stable CD4 positive cell line is selected for low marker background expression levels 40. Preferably, the marker gene is luciferase. An immortalized cell line 15 is positive for CCR5, CD4 and CXCR4 receptors and optionally other receptors illustratively including CCR3, CCR2B and T-lymphocyte expressed 7 transmembrane domain receptor. Preferably, the origin cell line is HeLa. More preferably, the cell line is J53 (Oregon Health Sciences University) or a cell line that naturally expresses CD4, CCR5 and CXCR4. The cells of immortalized cell line 15 are then tested for sensitivity to HIV-1 infection 25. Expansion of highly sensitive cells to HIV-1 infection 35. The clone of 40 is used to transduce 50 the highly sensitive immortalized cell line of 35. Preferably, the receptor is selected to create a cell which is highly sensitive to infection by HIV-1 isolates. Clones established from this second transduction are both highly sensitive to infection with primary HIV-1 isolates and express low background levels of the marker gene product in the absence of HIV-1 60. Those clones which are positive for the marker gene are identified 70. Such positive clones 70 have utility to promote HIV production upon transduction with Tat 75. HIV primary virus stock production is exploited herein to selectively enrich drug resistant minor HIV strains infecting a host 85.

Infection of the clones expressing low background levels of at least two markers such as β-gal and luciferase with HIV-1 confirms the relationship between infectious viral units and marker gene (luciferase) activity 80, although in practice expression of a single marker gene is operative herein. Clones that relate infectious virus units, such as β-gal, with a second marker gene activity such as luciferase find utility in the measurement of HIV co-receptor utilization (not shown). The cells capable of expressing marker genes in response to HIV infection are optionally used to measure viral sensitivity in the presence of a drug 90. Drug resistance to various pharmaceutical during viral life cycle events such as envelop formation 92, reverse transcription 94 and proteolysis 96 is optionally determined. The measurement of viral sensitivity finds utility in HIV viral target resistance analysis 98. The resulting composition of clones in a suitable medium is amenable for use to quantify HIV-1 titer. The present invention also finds utility in quantifying the drug sensitivity of particular HIV-1 phenotypes.

It is appreciated that the present invention is applicable to use with immunodeficiency viruses other than the representative HIV-1. By transducing a cell line to express co-receptors adapted for binding an immunodeficiency virus, a variety of viruses may be assayed with the present invention.

The present invention pertains to cell lines that are capable of detecting sensitivity of a given strain of HIV to inhibitors that act upon various stages of the virus life cycle by monitoring the effect various drugs have on early viral life cycle stages such as reverse transcription, integration and envelop mediated receptor binding, envelope fusion, as well as the late life cycle stages complexes such as proteolysis and Gag complex formation. A method and a kit are provided for monitoring the major and minor virus populations infecting a given host. Through the enrichment and detection of minor drug resistant virus populations and the sensitivity of those populations to viral inhibitors, the assay is well suited for determining specific anti-retroviral drugs suited to contain replication of the various HIV strains infecting a given host. Such a tailored therapeutic protocol is more effective in inhibiting viral amplification and/or reduces pharmacological side effects. In particular, the J53 Tat cell line is well suited to detect sensitivity of a host's particular viral infection to inhibit or affect the various stages of the virus life cycle. The present invention provides more rapid viral amplification as compared to conventional PBMC cells thereby allowing more rapid amplification, with fewer cycles of reverse transcription. Further applications of the present invention include measurement of HIV attributes of co-receptor utilization, antibody neutralization, isolation, titration, gene sequencing, and CTL assays.

The present invention also provides a method for detection of primary HIV from plasma, including noninfectious HIV-1 found in plasma. A loss of viral infectivity is due in part to a loss of env or env blocking. VSV-G serves to mediate infection of HIV-1 particles and thus, in the absence of VSV-G the virus remains noninfectious, whereas in its presence infectivity is complemented.

It is appreciated that in addition to VSV-G other infectivity complements are also operative herein including adenovirus, liposome, monoclonal antibody and other vectors to complement noninfectious HIV.

The methods and indicator cell lines of the present invention are operative to analyze drug sensitivity of primary HIV which has been purified and taken directly from infected host plasma.

To directly analyze the relationship between luciferase expression and infectious virus units, a series of gene transfer plasmids are constructed to express luciferase, β-galactosidase (β-gal), and green fluorescence protein (GFP), respectively. β-gal, GFP, and luciferase (luf) are placed under control of the HIV-1 or HIV-2 long terminal repeats (LTR), and the Rev Responsive Element (RRE). FIGS. 2A through 2E illustrate the different gene transfer expression plasmids that are constructed. The β-gal and GFP markers allow for direct enumeration of the number of infectious virus units as infected cells by counting under a microscope. The luciferase marker allows for sensitive and high throughput quantitation of HIV infection. In the present invention the requirement of Tat and Rev for marker gene expression is different from previous work in that it allows for highly regulated and decreased background level expression of the marker gene. This is particularly important for luciferase.

The J53BL cell line or its functional equivalents are operative in accordance with the present invention. It is appreciated that the nucleic acid sequences coding for CCR5, CXCR4, CD4, luciferase, β-galactosidase, GFP, CAT, Tat and the J53 cell line as a whole can be altered by substitutions, additions or deletions that provide for functionally equivalent cells. As used herein, "functional equivalency" is defined to mean a nucleic acid sequence which encodes for a product that performs operationally within the present invention with at least half the effectiveness of the product derived from the unaltered nucleic acid sequence of a receptor, amplicon, marker gene or cell line. Due to the degeneracy of nucleotide coding sequences, other DNA sequences which encode an substantially the same receptor amino acid sequences, cell line amino acid sequences, marker gene sequences and amplicon sequences may be used in the practice of the present invention. These include but are not limited to nucleotide sequences which are altered by the substitution of different codons that encode a functionally equivalent amino acid residue within the sequence thus producing a silent change. Likewise, receptor, marker, amplicon and cell lines proteins or fragments or derivatives thereof of the present invention include, but are not limited to, those containing as a primary amino acid sequence all or part of the amino acid sequence of the sequences for CCR5, CXCR4, CD4, luciferase, β-galactosidase, GFP, CAT, Tat and J53 sequences including altered sequences in which functionally equivalent amino acid residues are substituted for residues within the sequence resulting in a silent change. For example, one or more amino acid residues within a sequence are optionally substituted by another amino acid of a similar polarity which acts as a functional equivalent, resulting in a silent alteration. Substitutes for an amino acid within a sequence may be selected from other members of a class to which the amino acid belongs. For example, non-polar (hydrophobic) amino acids include alanine, leucine, isoleucine, valine, proline, phenylalanine, tryptophan and methionine. Polar neutral amino acids include glycine, serine, threonine, cysteine, tyrosine, asparagine and glutamine. The positively charged (basic) amino acids include arginine, lysine and histidine. Negatively charged (acidic) amino acids include aspartic acid and glutamic acid. Also included within the scope of the present invention are proteins or fragments or derivatives associated with J53BL which are differentially modified during or after translation by operations such as glycosilation, proteolytic cleavage and linkage to an antibody or other cellular ligand.

EXAMPLE 1

Generation of Transduction Vectors for the Delivery of Marker Genes

Figure 3:
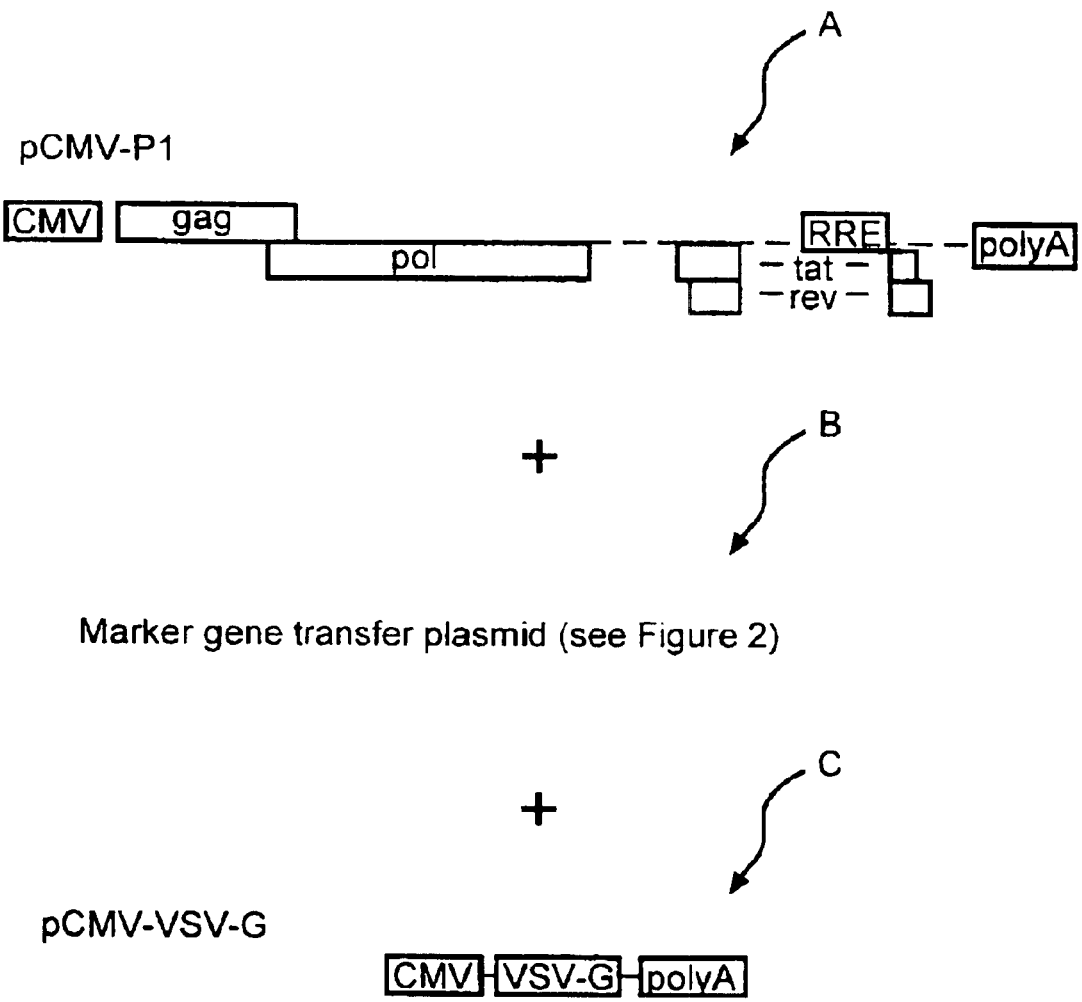
FIG. 3 is a schematic illustrating the production of lentiviral transduction vectors for the delivery of marker genes of the present invention. A gene transfer plasmid representatively including those shown in FIG. 2 are separately transfected into a host cell together with viral based packaging and envelope plasmids.
Figure 4A:
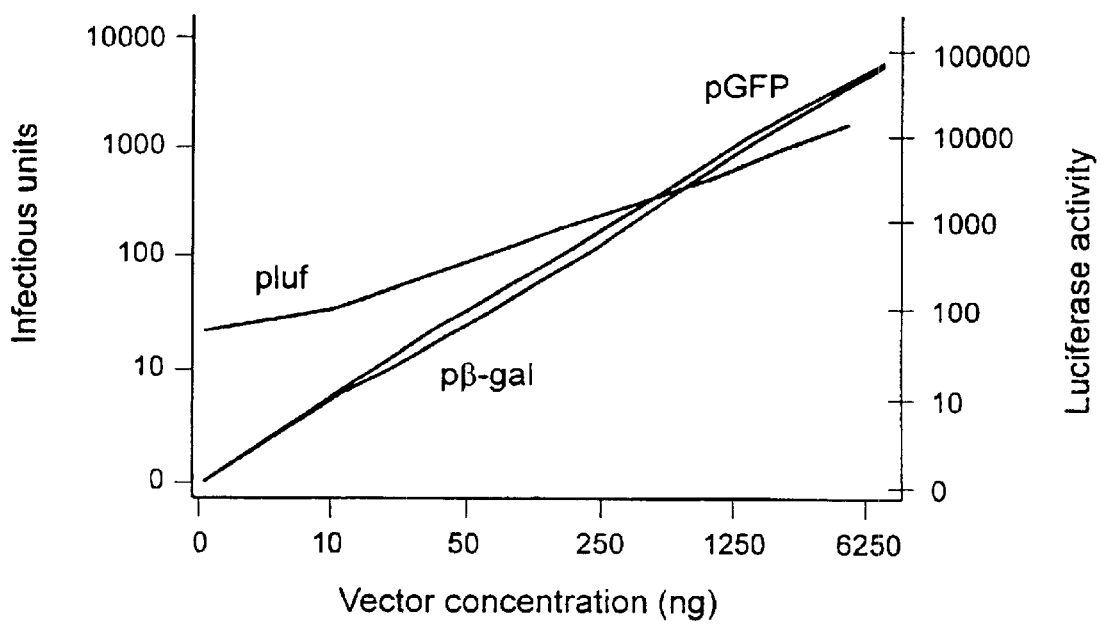
FIGS. 4A and 4B are graphs illustrating the relationship between the concentration of vector and infectious units as determined with β-gal, GFP and luciferase activity.
Figure 4B:
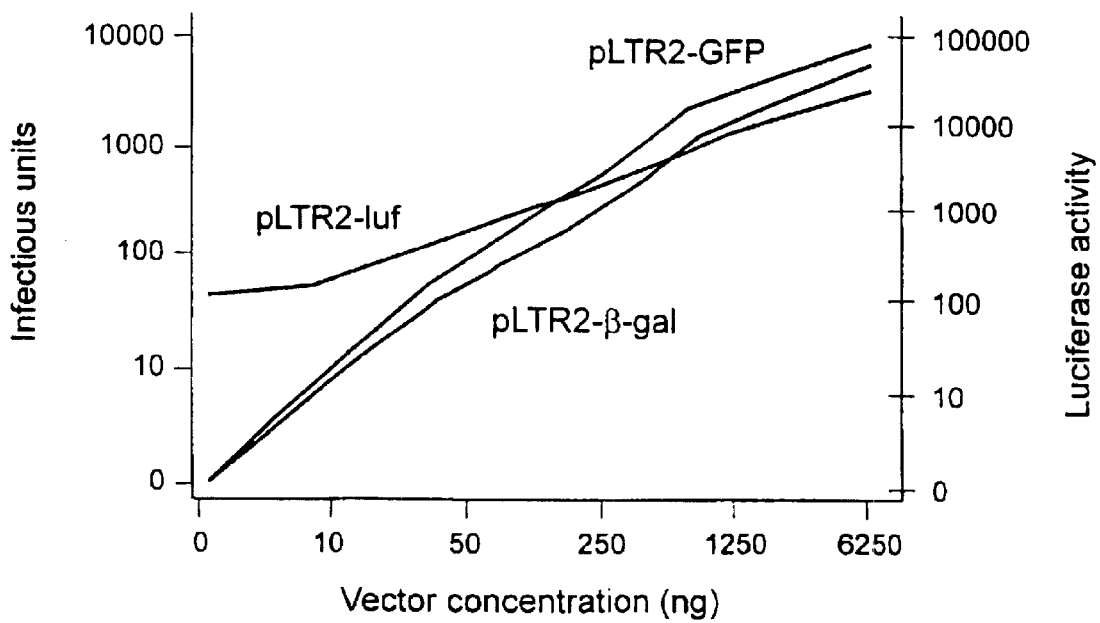

In order to generate vector stocks for transduction with the different reporter genes, the β-gal, GFP and luciferase gene transfer plasmids, including those containing the HIV-2 LTR (shown in FIG. 2), are separately transfected into cultures of 293T cell together with a lentiviral-based packaging plasmid (pCMV-GP1), and the pCMV-VSV-G env plasmid (FIG. 3). Forty-eight hours later, the vector-containing culture supernatants are harvested, clarified by low-speed centrifugation, filtered through 0.45 micron filters, analyzed for HIV-1 p24 core antigen concentration by ELISA, aliquoted, and cryopreserved as stocks. Four serial five-fold dilutions (normalized for p24 antigen concentration) of the stocks are prepared and used to infect replica cultures of HIV-HeLa cell. The HIV-HeLa cells contained an integrated HIV-1 provirus that is defective in vpr and env, and produces the Tat and Rev protein for transactivating marker gene expression. Two days after infection of the HIV-HeLa cells with the different vector stocks, β-gal and GFP expression is quantified using a microscope to count the number of positive cells/well. Luciferase expression is measured using standard assay methods (Promega) and a luminometer. FIGS. 4A and 4B show the relationship between concentration (HIV-1 p24 antigen, Coulter Inc.) of the vector stocks and infectious units as determined with β-gal and GFP, (virus infectious units) or luciferase activity.

EXAMPLE 2

Generation of β-gal, Luciferase and GFP Indicator Cell Lines to Quantify HIV/SIV Infection The following pairs of vector stocks (derived as described above) are used to co-transduce cultures of HeLa-CD4 cells: (a) pluf+pβ-gal, (b) pluf+pLTR2-β-gal, (c) pluf+pGFP, (d) pluf+pLTR2-GFP, (e) pLTR2-luf+pβ-gal, (f) pLTR2-luf+pLTR-2β-gal, (g) pLTR2-luf+pGFP, (h) pLTR2-luf+pLTR2-GFP. Three days later, the cells are biologically cloned by limiting dilution in 48 well plates. Wells containing clonal cells (confirmed after initial plating by microscopy) are expanded into replica cultures. One replica culture set is infected with HIV-1/SG3 and analyzed for marker gene expression (HIV-1 infection provided Tat and Rev to activate marker gene expression) as described above. Expression positive cells cultures are identified, expanded and cryopreserved.

Figure 5:
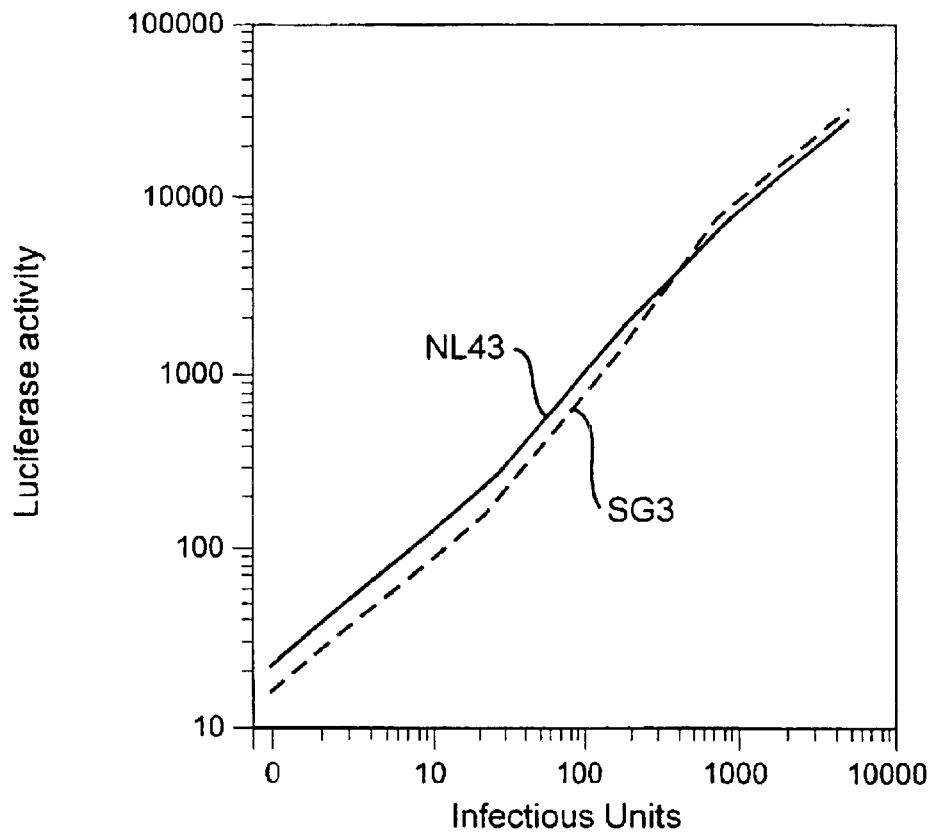
FIG. 5 is a graph illustrating a nearly linear relationship between HIV-1 infectious units and luciferase activity for a cell line of the present invention.

Since the expression of relatively few molecules of luciferase produces substantial luciferase activity levels, 36 non-HIV-1 infected, luciferase expression-positive clonal cultures (derived from HeLa-CD4 cells transduced with pluf+pβ-gal) are analyzed for luciferase activity to determine basal background expression levels. The HeLa-CD4 cells being obtained from the AIDS Research and Reference Reagent Repository of NIH. Of the 36 clones analyzed, luciferase activity ranged from 15 to 250 units. Analysis for β-gal expression in response to HIV-1 infection indicated approximately 70% of the clones expressed both β-gal and luciferase. The two clones (referred to as HeLa-β-gal-luf1, and HeLa-β-gal-luf2) that exhibited the lowest background levels of luciferase expression and are positive for β-gal expression are used to directly analyze the relationship between HIV-1 infectious units and luciferase activity. Serial dilutions of two different HIV-1 strains (HIV-1/SG3 and HIV-1/NL43) are normalized for p24 antigen concentration and used to infect replica cultures of HeLa-β-gal-luf1, and HeLa-β-gal-luf2. After 48 hours, one set of cultures is analyzed for luciferase activity and the other was analyzed for β-gal. FIG. 5 shows the relationship between HIV-1 infectious units (β-gal positive cells) and luciferase activity for the HeLa-β-gal-luf1 cell line. The HeLa-β-gal-luf2 cell line gave nearly identical results with slightly higher luciferase activity levels at the lower virus inoculums. Between approximately 10 and 10,000 virus infectious units. A near-linear relationship to luciferase activity is shown in FIG. 5. The linear range of detection using the luciferase marker in FIG. 5 is approximately 3 orders of magnitude, and as few as 10–20 infected cells out of approximately 100,000 can generate a virus-positive (above background) result. As referred to herein "near linear" is intended to mean an increase in marker activity, A proportional to an increase in the surrounding virus infectious unit concentration, IU such that $A=n(IU)^{1\pm x}+b$ where n is a real number; x is a real number between 0 and 0.5; b is the measured background level of marker expression in the absence of virus; for at least 2 orders of magnitude of IU. This dynamic range allows for quantitative analysis of virus infection from approximately 10 to 10000 infectious units, thereby reducing the necessity of dilution of virus in order to generate quantitative data.

EXAMPLE 3

Sensitive Detection of HIV-1 Primary Viruses Using β-gal and Luciferase Reporter Genes The present invention utilizes a combination of a reporter assay system for sensitively and rapidly quantifying infectious HIV-1 over a wide linear range with a cell line which is highly sensitive to infection with both M-tropic and T-cell tropic viruses. Transduction of the CD4-CCR5 positive J53 cell clone (Dr. David Kabat, Oregon Health Sciences University, Portland, Oreg.) with the pluf and pβ-gal expression vectors as described above. The pluf and pβ-gal transduced J53 cells (termed J53-βgal/luf) are infected with six different virus isolates (using four five-fold serial dilutions) that were unable to efficiently infect other CD4, CXCR4 expressing cell lines (P4 or Hi5) or a CD4, CXCR4 expressing cell line (MAGI) (see Table 2). Table 1 shows that all viruses, including the macrophage tropic YU2 clone, included as a control, are highly infectious in the J53β-gal/luf cell line.

Figure 6:
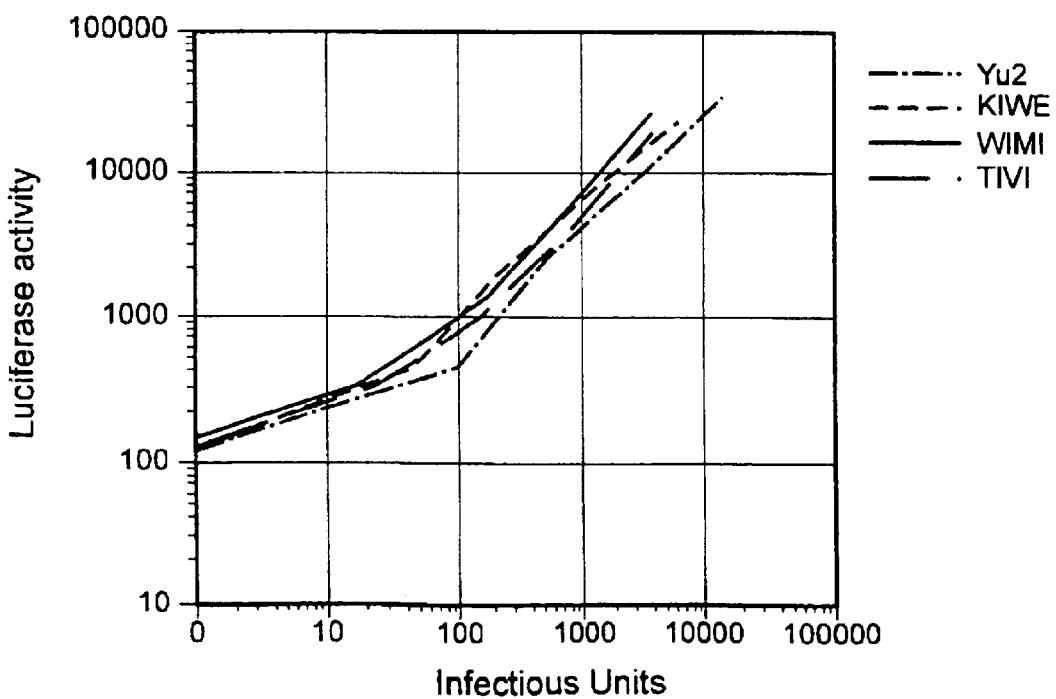
FIG. 6 is a graph illustrating the relationship between infectious virus units and luciferase activity for viruses: TIVI, WIMI, KIWE and YU2, using a cell line of the present invention.

To assess the relationship between infectious virus units and luciferase activity in the J53β-gal/luf cell line, four serial five-fold dilutions of the following viruses are prepared and analyzed: TIVI, WIMI, KIWE and YU2. Between approximately 100 to 10,000 infectious units, the data show a linear relationship with luciferase activity (FIG. 6). Background levels of luciferase are between 100 and 150. The J53β-gal/luf cell line represents a transduced population of cells since integration of the transduction vector into the genome of the J53 cells can occur differently in each cell.

To minimize luciferase background levels of non HIV induced expression and thus maximize sensitivity using luciferase as a reporter for HIV infection, cultures of single cell clones are derived from the J53β-gal/luf cell line as described above and characterized for luf and β-gal expression in response to HIV-1 infection. Ten clones expressing between 17 and 750 luf activity are selected for analysis. Clone number 13, termed J53-C13, is confirmed to express both luciferase and β-gal, and is used for subsequent analysis as described below. Stocks of twenty different HIV-1 isolates are obtained from HIV-1 infected individuals by standard coculture techniques. Each stock is analyzed for HIV-1 p24 antigen concentration, SI and NSI phenotype, and infectivity in HeLa-CD4 (MAGI), HeLa-CD4-CCR5 (P4), H9 CD4-CCR5 (Hi5), and HeLa-CD4-CCR5 (J53-C13) cells. These results are summarized in Table 2.

These results show that the J53-C13 cell line is sensitive to primary HIV-1. Importantly, the J53-C13 cell line is sensitive to HIV-1 infection to a degree similar to PBMC. To confirm the importance of the CCR5 co-receptor for this level of sensitivity, the JC11 cell line is analyzed for comparison. JC11 is the parental cell line to J53-C13. It expresses equal amounts of CD4 and CXCR4 but is negative for CCR5. JC11 is transduced to express b-gal and luciferase, and positive cells are biologically cloned exactly as described above for J53-C13. A clone designated J11-C5, which is capable of expressing both b-gal and designated J11-C5, which is capable of expressing both b-gal and luciferase, is selected for comparison with J53-C13. Both cell lines are infected with primary virus isolates and molecularly cloned virus including YU2, SG3, and 89.6 (a dual tropic crone). Table 4 shows the titer of each virus in the J53-C13 and J11-C5 cell lines. The results show a marked reduction in virus titer in the J11-C5 cell line, indicating that the CCR5 co-receptor is necessary for efficient infection/detection of primary virus isolates.

Figure 7:
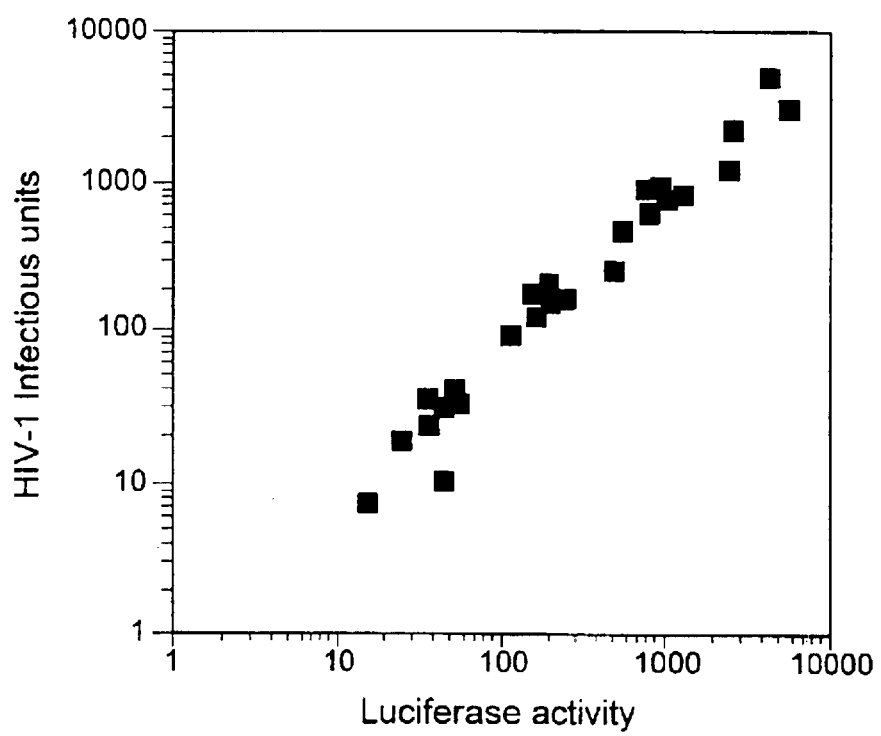
FIG. 7 is a graph illustrating a correlation between infectious virus units and luciferase activity.

To analyze the relationship between luciferase and β-gal expression over a range of different virus concentrations, 5-fold serial dilutions are prepared from seven different virus stocks and used to infect J53-C13 cells. After two days the number of β-gal positive cells and luciferase activity is determined. FIG. 7 shows a strong correlation (r=0.92) between β-gal positivity (infectious virus units) and luciferase activity over 2 orders of magnitude.

EXAMPLE 4

Figure 8A:
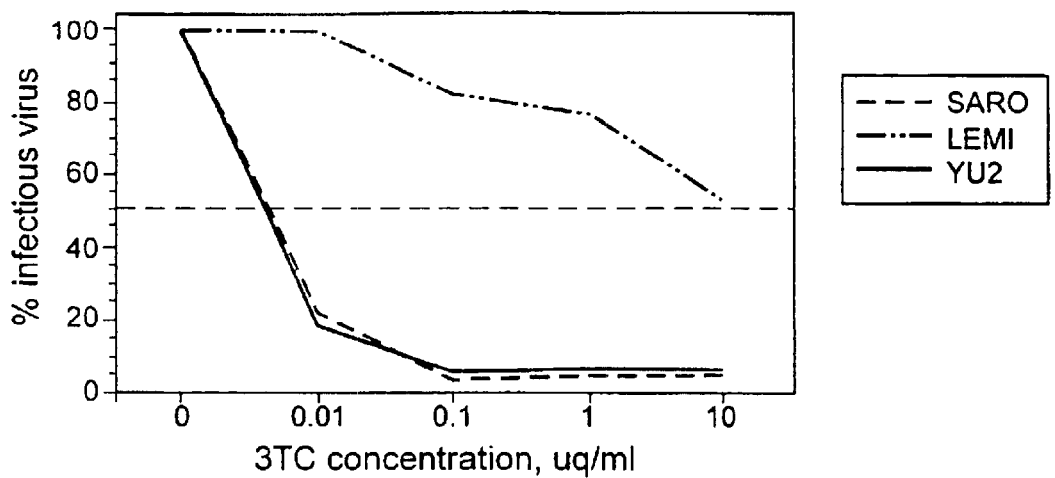
FIGS. 8A–8C are graphs illustrating the effect that different concentrations of 3TC, AZT, and Nevaripine, respectively, have on virus replication relative to non-drug treated viruses as determined by luciferase activity according to the present invention.
Figure 8B:
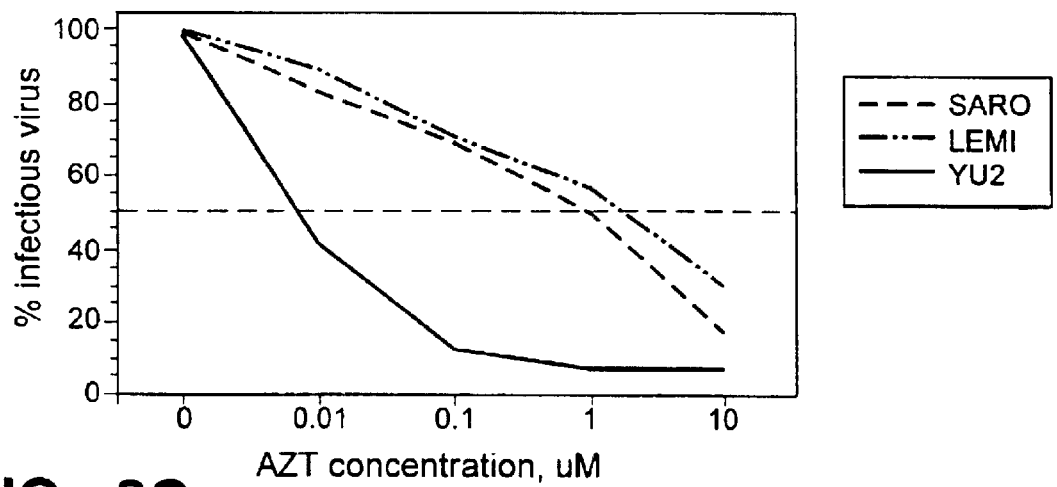
Figure 8C:
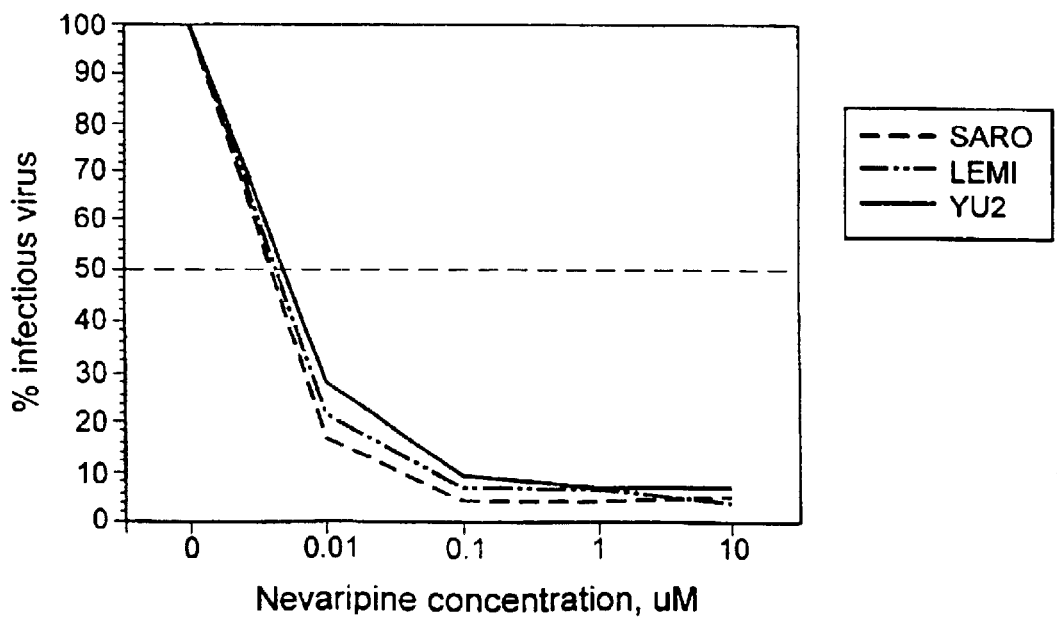

Evaluation of Primary HIV-1 Isolates for Drug Sensitivity/resistance Using the J53β-gal/luf (J51-C13) Cell Line HIV-1 isolates are derived by PBMC coculture from two different HIV-1 infected patients (LEMI and SARO) receiving anti-retroviral treatment. The RT sequence of each isolate is analyzed for nucleic acid sequence using ABI sequencing methods. Known drug resistance conferring mutations found in the LEMI and SARO RT sequences are shown in Table 3. The LEMI and SARO and YU2 (included as a control) virus stocks are used to infect the J53-C13 reporter cell line in the presence of AZT, 3TC and Nevaripine (NVP), respectively. Two days after infection the cells are lysed and the clarified lysates are examined for luciferase activity using standard methods (Promega). FIG. 8 shows the effect of different concentrations of drug on virus replication relative to non-drug treated viruses—as determined by luciferase activity as an indicator.

Figure 9A:
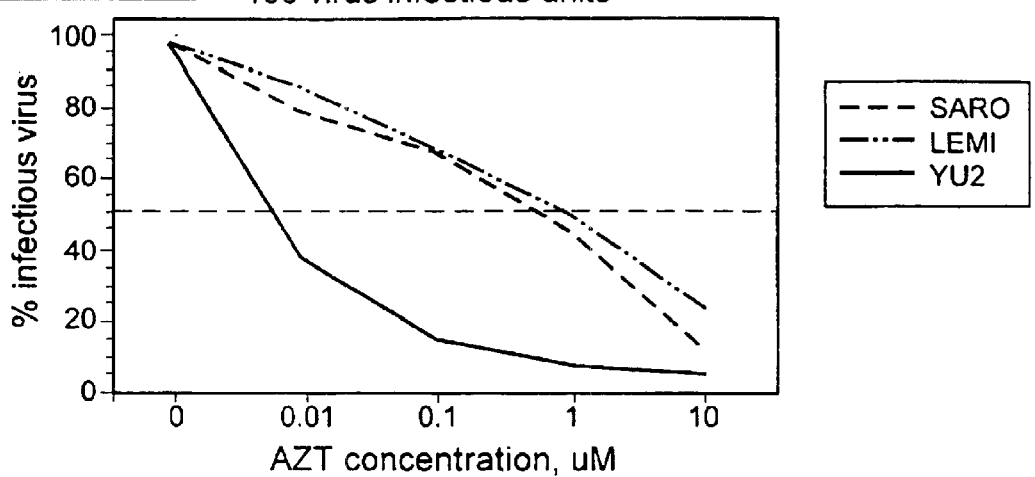
FIGS. 9A–9C are graphs illustrating drug sensitivity to AZT for 100, 500, and 2500 virus infectious units respectively, according to the present invention.
Figure 9B:
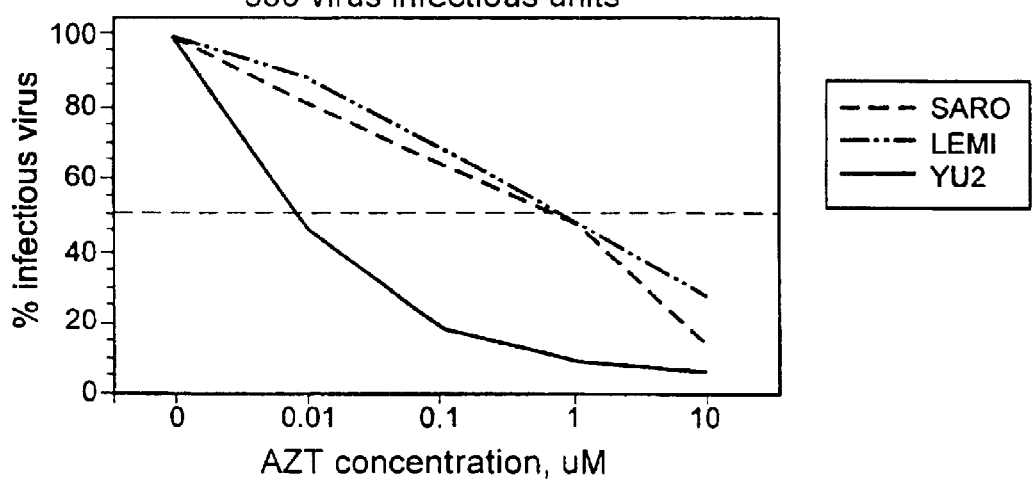
Figure 9C:
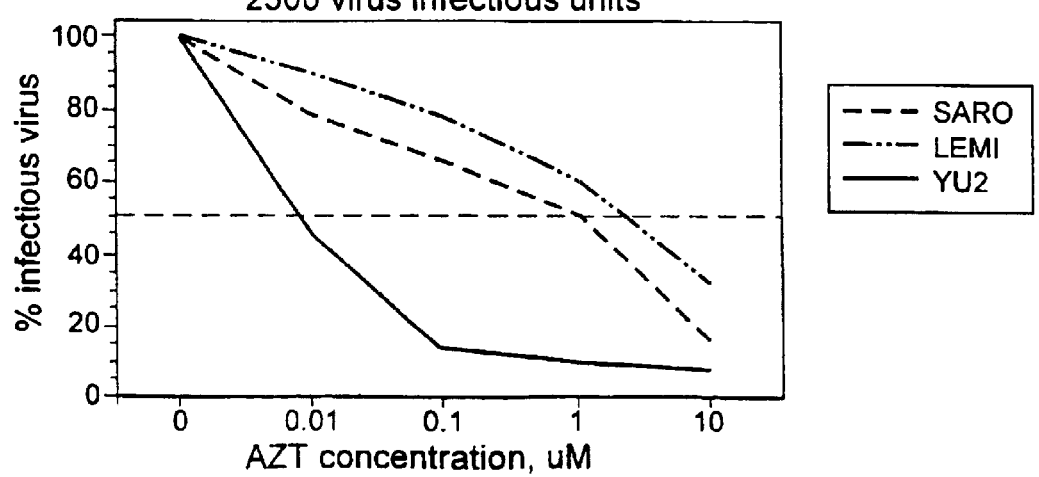

A major problem with existing methods for evaluating HIV-1 drug sensitivity is that differences in virus inoculum can have significant effects on the IC50 for a given drug. That is, as the infectious dose of virus is increased, the concentration of drug that inhibits virus replication by 50% is increased. This factor has made drug sensitivity testing extremely difficult to standardize among independent laboratories. J53-C13 cells are infected with 100, 500, and 2500 infectious units of virus and analyzed for drug sensitivity as described above. FIG. 9 shows the results for drug sensitivity to AZT. There is no significant shift in the IC50 among the different drug concentrations tested. Analysis of 3TC and Nevaripine showed similar results (data not shown).

EXAMPLE 5

Figure 10:
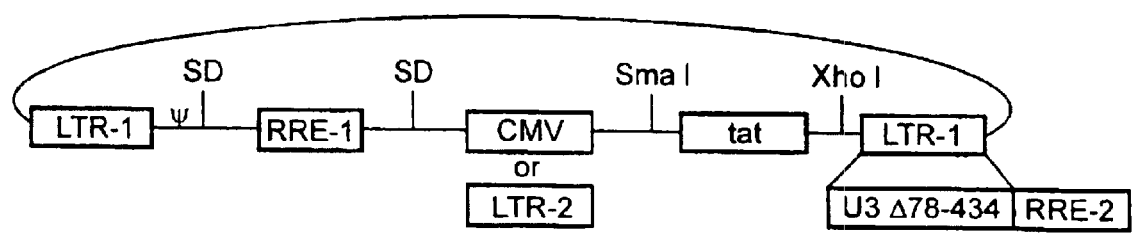
FIG. 10 is a schematic illustrating the construction of a Tat transduction plasmid.

Generation of a Tat Expressing Cell Line to Rapidly Amplify Virus Production from Infected Cells The amplification of primary virus from infected individuals is required for phenotypic resistance in assays that test whole virus. Currently, the only effective means by which this can be accomplished is by culture of infected tissue with donor PBMC. The present invention confirms that the JC53 and the J53-C13 cell lines are highly sensitive to infection of primary virus isolates. Thus, these cell lines may be utilized to amplify the primary virus isolate instead of PBMC. To this end, JC53 cells are transduced with the HIV Tat gene under control of the CMV, or LTR promoter, as shown in FIG. 10. To eliminate Tat transactivation of the lentivirus vector LTR, Tat is constructed into a self-deleting U3 transduction vector, FIG. 10. Three days after transduction, single cells are cloned and 33 are identified to be Tat expression positive, 10 containing LTR-2 as a promoter and 23 containing CMV as a promoter for Tat expression. To identify which of these clones could most efficiently promote HIV-1 replication, HIV-1 YU2 is used for infection at an MOI=0.01. After 40 hrs. virus production is measured by HIV-1 p24 antigen ELISA and the highest HIV-1 producing lines from each are selected for further analysis. The highest HIV-1 producer, designated J53-CMVtat is infected with the YU2 clone and the KEWI virus isolate at MOIs of approximately 0.1. As a control, the JC53 cell line is analyzed in a parallel experiment. 40 hrs. later culture supernatants are analyzed for HIV-1 production by p24 antigen ELISA. The results, shown in Table 5, indicate that the Tat expressing cell lines causes a 4-6-fold increase in HIV-1 replication.

EXAMPLE 6

Figure 11A:
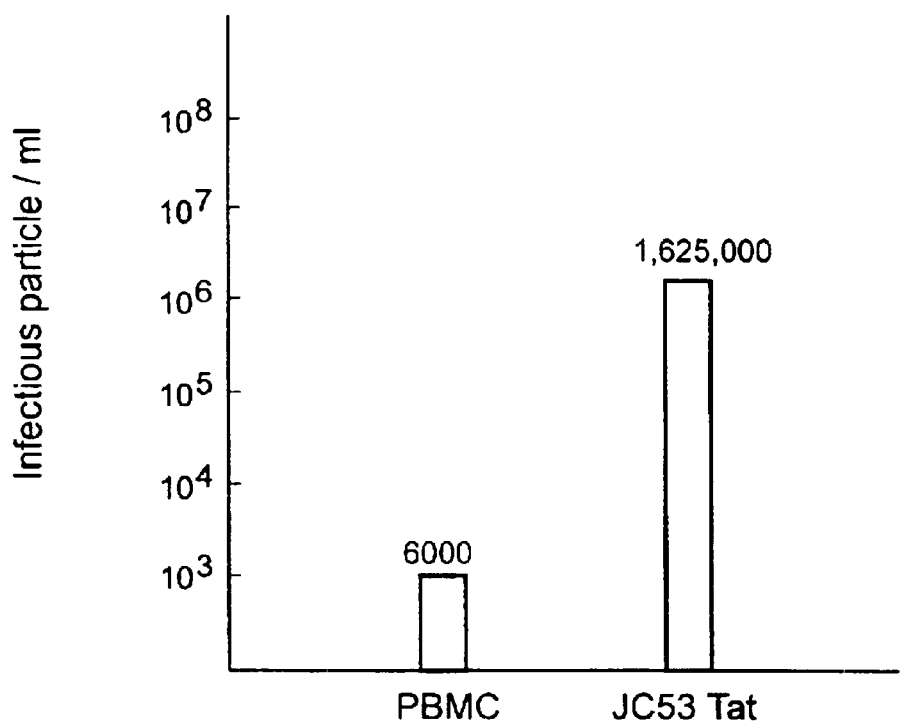
FIGS. 11A and 11B are graphs illustrating the viral amplification two days following infection with equal quantities of YU2 HIV (a) for infectivity and (b) p24 antigen.
Figure 11B:
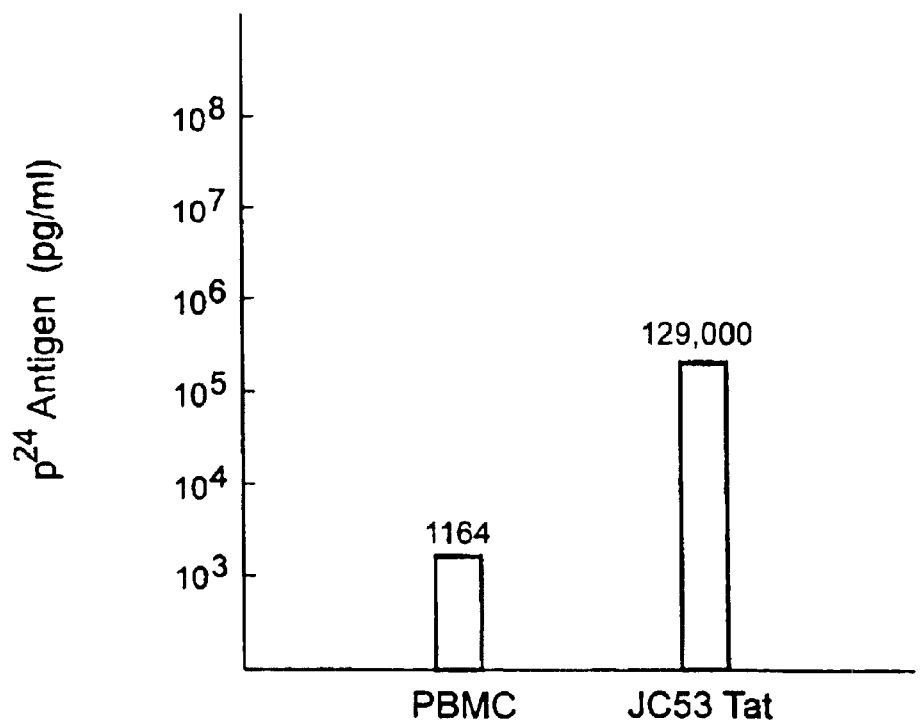

The Use of CD4/CCR5/CXCR4+Tat Expressing Cell Line to Capture and Amplify Primary Virus The J53tat cell line is compared with PBMC for primary virus amplification. PBMC and J53tat are each infected with 2.5E5 infective particles of YU2. Two days later the concentration of progeny virus is analyzed for infectivity in J53BL indicator cells as shown in FIG. 11($a$) and by p24 antigen ELISA, as shown in FIG. 11($b$). The J53tat cell line amplifies primary virus to higher titers and more rapidly than PBMC. Since the parental J53BL cell line is highly sensitive to primary virus, Tat facilitates the rapid generation of high titered primary virus stocks for resistance testing without selection of longer term culture, such as PBMC culture for virus amplification.

EXAMPLE 7

Detection of Drug Resistance/sensitivity that Effect Various Stages of Virus Life Cycle The J53tat cell line is used to produce virus and thereby enable viral testing of drug candidates that affect various stages of the virus life cycle. Thus, viral drug resistance mutations in early stage targets such as reverse transcriptase (RT), integrase (IN) and env; and late stage targets such as protease and Gag are analyzed by the methods of the present invention. The J53tat cells are infected with HIV YU2 (MOI of either 0.2 or 0.04), and protease inhibitor (indinavir) is added to the cultures at various concentrations. Forty hours after infection the culture supernatant is collected and used to infect the J53BL cell line in the presence of the same drug concentrations. Table 6 shows that YU2 is sensitive to protease inhibitor, with increasing concentrations causing greater inhibition.

EXAMPLE 8

Detection of Noninfectious Cultured Virus

To test how to recover noninfectious virus, a molecular clone is generated to produce env minus HIV-1 (pSG3-env).

SG3-env virus, derived by transfection, is mixed (1:2, v:v) with VSV-G derived from the supernatant of pDm transfected 293T cell cultures. The mixture is ultracentrifuged for 1.5 hours at 1 15,000g at 4° C. The pellet is resuspended in 100 ul DMEM. The infectivity is then determined using J53BL cells. The infectivity is determined to be 7.5E4. Without mixing of VSV-G the infectivity is 0.

YU2 virus containing wild-type envelope is pelleted through sucrose by ultracentrifugation to strip away the gp120 glycoprotein (SU). The resuspended (100 ul) virus is mixed with and without VSG-G (1:1) and repelleted by ultracentrifugation (150,000 g, 2 hours, 4° C.). The pellets are resuspended in 100 ul DMEM, and the infectious units are determined using J53BL cell summarized as in Table 7. Virus pelleted through sucrose is noninfectious. Virus pelleted through sucrose, mixed with VSV-G and repelleted had a marked increase in infectivity. The recovery in infectivity is approximately 20% compared with the original virus stock.

EXAMPLE 9

Detection of Noninfectious Plasma Virus

Patient plasma (GADA) is mixed with and without VSV-G, pelleted through sucrose, resuspended in 100 ul DMEM as per Example 10. Infectivity is measured using J53BL cells. Without VSV-G 1500 infectious particles are detected. With VSV-G 2500 infectious particles are detected as summarized in Table 7.

EXAMPLE 10

Detection of Plasma Virus Using CD4/CCR5/CXCR4 or CD4/CCR5/CXCR4+Tat Expressing Cell Line to Capture and Amplify Primary Virus Plasma from patients infected with HIV-1 is tested for the presence of infectious virus in the plasma towards J53BL cells. Three serial dilutions of plasma are incubated with J53BL cell line for 4 hours. Three days later the cells are stained for β-gal and infectious units are counted by microscopy as summarized in Table 8.

EXAMPLE 11

Integrated HIV Genome Expansion with Limited Rounds of Reverse Transcription HIV is incubated with J53BL cell line for four hours to allow binding and entry into J53BL cells, reverse transcription proceeds and the viral cDNA is integrated into the chromosomes of J53BL cells. Thereafter, HIV replication is suppressed through expression of an inhibitor of viral gene expression, such as the rev inhibitor, rev m10 by conventional techniques. The HIV genome is expanded as J53BL cells divide and increase in number, without further rounds of reverse transcription. The increased copy numbers of the viral genome are purified and sequenced. By relieving the inhibitory effect on rev, viral gene expression will return to normal in the expanded cells, and virus can be analyzed.

Based on the description and examples of the present invention, it is appreciated that modifications of the present invention will be apparent to one skilled in the art of the present invention. Such modifications are intended to fall within the scope of the appended claims.

All references cited herein are intended to be incorporated to the same extent as if each reference was individually incorporated by reference.

TABLE 1

Efficient HIV-1 infection of a CD4 CCR5 expressing HeLa cell line.

| HIV-1 isolate[a] | p24 pg/ml | PBMC[b] | HeLa-CD4-CCR5[c] |
|---|---|---|---|
| KEWI | 2.64E + 05 | 4.58E + 04 | 2.30E + 05 |
| WIMI | 1.31E + 05 | 1.15E + 04 | 8.10E + 04 |
| SMBA | 5.34E + 05 | 4.58E + 04 | 1.60E + 05 |
| CHVI | 6.50E + 04 | 1.15E + 04 | 7.00E + 04 |
| DECH | 2.07E + 05 | 4.58E + 04 | 1.30E + 05 |
| TIVI | 1.20E + 05 | 1.84E + 05 | 4.20E + 05 |
| YU-2 | 6.20E + 05 | 7.36E + 05 | 5.10E + 04 |

[a]HIV-1 isolates were derived by coculture (7–10 days) of HIV-1 infected patient PBMC with PHA stimulated normal donor BPMC.
[b]Virus titer-determined by endpoint dilution titration in PBMC, calculated by the Spearman-Karber Formula (TCID 50/ml)
[c]Virus titer-determined by counting the number of virus infected (blue) HeLa-CD4-CCR5-β-gal indicator cells (J53-C16).

TABLE 2

Comparison of HIV-1 isolate infectivity in different cell types

| HIV-1 isolate | HeLa-CD4 (MAGI cells) | HeLa-CD4-CCR5 (P4 cells) | H9 CD4-CCR5 (Hi5 cells) | HeLa-CD4-CCR5 (J53-C16) | PBMC | Syncytia phenotype |
|---|---|---|---|---|---|---|
| IVED 1563 | 2.10E + 02 | 2.24E + 03 | <1.2E + 2 | 2.2E + 4 | 1.84E + 05 | NSI |
| SHTI 2045 | 2.00E + 01 | 5.72E + 02 | 2.88E + 03 | 1.2E + 5 | 4.58E + 04 | SI |
| RIJA 0676 | 1.50E + 01 | 1.68E + 02 | <1.2E + 2 | 4.5E + 5 | 1.84E + 05 | SI |
| ELRA 1452 | 1.50E + 01 | 1.00E + 02 | <1.2E + 2 | 9.5E + 5 | 4.58E + 04 | NSI |
| JAME 2457 | 5.00E + 00 | 4.00E + 00 | <1.2E + 2 | 1.8E + 5 | 4.58E + 04 | SI |
| WOAL 0263 | 1.80E + 01 | 5.40E + 02 | <1.2E + 2 | 8.5E + 4 | 4.58E + 04 | SI |
| WIMI 2294 | 2.10E + 01 | 1.52E + 02 | <1.2E + 2 | 4.53 + 4 | 1.15E + 04 | SI |
| DAKE 2205 | 6.20E + 01 | 3.28E + 02 | <1.2E + 2 | 1.1E + 5 | 4.58E + 04 | NSI |
| BARE 1219 | 1.80E + 01 | 4.48E + 02 | <1.2E + 2 | 1.3E + 5 | 4.58E + 04 | NSI |
| SMBA 1685 | 2.20E + 01 | 6.40E + 01 | <1.2E + 2 | 1.1E + 5 | 4.58E + 04 | SI |
| TIVI 2007 | 8.90E + 01 | 4.60E + 02 | <1.2E + 2 | 4.1E + 5 | 1.84E + 05 | SI |

TABLE 2-continued

Comparison of HIV-1 isolate infectivity in different cell types

| HIV-1 isolate | HeLa-CD4 (MAGI cells) | HeLa-CD4-CCR5 (P4 cells) | H9 CD4-CCR5 (Hi5 cells) | HeLa-CD4-CCR5 (J53-C16) | PBMC | Syncytia phenotype |
|---|---|---|---|---|---|---|
| SWBA 1427 | 2.80E + 01 | 4.48E + 02 | <1.2E + 2 | 9.0E + 4 | 4.58E + 04 | NSI |
| CHVI 2467 | 5.00E + 01 | 4.00E + 00 | <1.2E + 2 | 3.8E + 4 | 1.15E + 04 | SI |
| VIJE 1945 | 7.80E + 01 | 3.04E + 02 | 2.88E + 03 | 2.1E + 5 | 4.58E + 04 | NSI |
| DECH | 1.20E + 01 | 2.00E + 01 | <1.2E + 2 | 1.2E + 5 | 4.58E + 04 | NSI |
| SHCH | 1.80E + 02 | 1.76E + 04 | <1.2E + 2 | 3.6E + 5 | 4.58E + 04 | NSI |
| PELE 1256 | 1.20E + 01 | 2.40E + 01 | 2.88E + 03 | 1.0E + 5 | 1.15E + 04 | SI |
| KEWI 2431 | 1.90E + 03 | 4.54E + 05 | <1.2E + 2 | 2.0E + 5 | 4.58E + 04 | NSI |
| MADA 2442 | 2.00E + 01 | 1.40E + 03 | <1.2E + 2 | 2.8E + 5 | 4.58E + 04 | NSI |
| VATE 2328 | 2.00E + 01 | 3.76E + 02 | <1.2E + 2 | 4.5E + 4 | 1.15E + 04 | SI |
| SG3-293T | 2.20E + 05 | 1.89E + 05 | 1.84E + 05 | 2.0E + 5 | 1.84E + 05 | SI |
| YU-2-293T | 0.00E + 00 | 3.50E + 05 | 4.58E + 04 | 5.9E + 4 | 7.36E + 05 | NSI |

TABLE 3

RT resistance conferring mutations

| | YU2 | SARO | LEMI |
|---|---|---|---|
| AZT | | M41L | |
| | | D67N | D67N |
| | | | K70R |
| | | T215Y | |
| | | | K219Q |
| 3TC | | | M184V |

TABLE 4

CCR5 facilitates infection of primary isolates of HIV-1

| Virus Stock | J53-C13 titer | J11-C5 titer |
|---|---|---|
| DBP D-7 | 6.30E + 04 | Neg. |
| DBP d140 | 1.20E + 04 | 4.00E + 01 |
| HVH D-7 | 6.10E + 04 | 1.10E + 04 |
| HVH D140 | 6.80E + 04 | 1.00E + 03 |
| SHL D-7 | 6.00E + 04 | Neg. |
| SHL D140 | 7.70E + 04 | Neg. |
| TED D127 | 1.30E + 05 | Neg. |
| TED D211 | 3.20E + 04 | Neg. |
| XHB2 | 1.75E + 05 | Neg. |
| YU2 | 4.85E + 05 | 7.50E + 04 |
| 89.6 | 1.40E + 05 | Neg. |

Virus titer was determined by counting the # of beta-gal positive cells. Results indicate infection positive cells per ml of stock virus. Neg. (negative) titers were undetectable below 40 infectious units per ml.

TABLE 5

Trans Tat expression enhances HIV-1 production

| | JC53 | | JC53-CMVtat | |
|---|---|---|---|---|
| Virus | Exp. 1. | Exp. 2 | Exp. 1 | Exp. 2 |
| YU2 | 1240 | 920 | 6430 | 4910 |
| KEWI | 3120 | 2760 | 9590 | 7590 |

Nos. represent pg of p24 antigen per ml.

TABLE 6

Number of colony formed in the presence of protease Inhibitor Indinavir

| | INDINAVIR | | | | |
|---|---|---|---|---|---|
| | 0 MM | 0.008 MM | 0.04 MM | 0.2 MM | 1.0 MM |
| 0.2 M.O.I | >1000 | >1000 | 343 | 99 | 0 |
| 0.04 M.O.I | 198 | 105 | 2 | 2 | 0 |

TABLE 7

| Conditions | Recovery (%) |
|---|---|
| No sucrose, no VSV-G | 0.006 |
| Sucrose, no VSV-G | 0 |
| Sucrose, VSV-G | 20 |

TABLE 8

Detection/Isolation of HIV-1 from human plasma using J53BL cells

| Plasma virus | TCIU/PBMC | TCIU/J53 BL |
|---|---|---|
| LEMI | $3.47 \times 10^3$/m | $4.40 \times 10^3$/ml |
| ALPI | $3.47 \times 10^3$/m | $1.20 \times 10^4$/ml |
| GADA | $7.81 \times 10^3$/ml | $1.20 \times 10^4$/ml |

TCIU = tissue culture infectious units

What is claimed is:

1. A cell deposited as Patent Deposit No. PTA-5659.
2. A method for detecting HIV virus comprising:
   a) providing a cell deposited as Patent Deposit No. PTA-5659;
   b) contacting said cell with a composition; and,
   c) assaying for marker gene expression—wherein expression of said marker gene indicates that—HIV is present in said composition.
3. The method of claim 2, wherein marker gene expression quantitates the level of infectious HIV units.
4. The method of claim 2, further comprising isolating said HIV.
5. The method of claim 2, wherein said HIV is a primary HIV.
6. The method of claim 5, wherein said primary HIV is a HIV-1.
7. A kit comprising a cell deposited as Patent Deposit No. PTA-5659.

* * * * *

UNITED STATES PATENT AND TRADEMARK OFFICE
CERTIFICATE OF CORRECTION

PATENT NO.     : 6,797,462 B1
DATED          : September 28, 2004
INVENTOR(S)    : Kappes et al.

It is certified that error appears in the above-identified patent and that said Letters Patent is hereby corrected as shown below:

<u>Title page, Item [54], and Column 1, lines 1-3,</u>
Title, "CELL-BASED ASSAY FOR IMMUNODEFICIENCY VIRUS INFECTIVITY AND SENSITIVITY" should read -- CELL-BASED METHOD AND ASSAY FOR MEASURING THE INFECTIVITY AND DRUG SENSITIVITY OF IMMUNODEFICIENCY VIRUS --.

Signed and Sealed this

Twenty-first Day of December, 2004

JON W. DUDAS
*Director of the United States Patent and Trademark Office*